(12) United States Patent
Wang et al.

(10) Patent No.: US 7,102,747 B2
(45) Date of Patent: Sep. 5, 2006

(54) IN SITU EXCITATION FOR SURFACE ENHANCED RAMAN SPECTROSCOPY

(75) Inventors: Shih-Yuan Wang, Palo Alto, CA (US); Zhiyong Li, Palo Alto, CA (US); M. Saif Islam, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 142 days.

(21) Appl. No.: 10/964,523

(22) Filed: Oct. 13, 2004

(65) Prior Publication Data

US 2006/0077382 A1    Apr. 13, 2006

(51) Int. Cl.
*G01J 3/44* (2006.01)
*G01N 21/65* (2006.01)

(52) U.S. Cl. ..................................... 356/301
(58) Field of Classification Search ................. 356/301
See application file for complete search history.

(56) References Cited

U.S. PATENT DOCUMENTS

| | | | |
|---|---|---|---|
| 5,119,460 A | 6/1992 | Bruce et al. | |
| 5,166,940 A | 11/1992 | Tumminelli et al. | |
| 5,835,231 A | 11/1998 | Pipino | |
| 6,438,150 B1 | 8/2002 | Yoo | |
| 6,448,064 B1 | 9/2002 | Vo-Dinh et al. | |
| 6,558,958 B1 | 5/2003 | Pilevar et al. | |
| 6,621,836 B1 | 9/2003 | Karwacki | |
| 6,643,305 B1 | 11/2003 | Bewley et al. | |
| 6,678,300 B1 | 1/2004 | Johnson et al. | |
| 2002/0068018 A1 | 6/2002 | Pepper et al. | |
| 2002/0093651 A1 | 7/2002 | Roe | |
| 2002/0159736 A1 | 10/2002 | Dejneka et al. | |
| 2003/0059820 A1 | 3/2003 | Vo-Dinh | |
| 2004/0160606 A1* | 8/2004 | Lakowicz et al. | ........ 356/445 |

OTHER PUBLICATIONS

Bour, David P., et al., "Characteristics of InGaN-AlGaN Multiple-Quantum-Well Laser Diodes," IEEE Journal of Selected Topics in Quantum Electronics, vol. 4, No. 3, May/Jun. 1998, pp. 498-504.
Chang-Hasnain, Connie J., "Tunable VCSEL," IEEE Journal on Selected Topics in Quantum Electonics, vol. 6, No. 6, Nov./Dec. 2000.
Emory, Steven R., et al., "Near-Field Surface-Enhanced Raman Spectroscopy on Single Silver Nanoparticles," Anal. Chem., vol. 69, No. 15, Jul. 15, 1997, pp. 2631-2635.
Kneipp, Katrin, et al., "Single Molecule Detection Using Surface-Enhanced Raman Scattering (SERS)," Physical Review Letters, vol. 78, No. 9, Mar. 3, 1997, pp. 1667-1670.
Nie, Shuming, et al., "Optical Detection of Single Molecules," Annu. Rev. Biophys. Biomol. Struct., 1997, vol. 26, pp. 567-596.
Nie, Shuming, et al., "Probing Single Molecules and Single Nanoparticles by Surface-Enhanced Raman Scattering," Science, vol. 275, Feb. 21, 1997, pp. 1102-1106.

(Continued)

Primary Examiner—F. L. Evans

(57) ABSTRACT

Devices, systems, and methods using Surface Enhanced Raman Spectroscopy (SERS) are disclosed. A device for generating Raman scattered radiation comprises a laser source and a SERS-active structure. The laser source may be configured for emanating radiation from an emanating surface or by forming a depression in the laser source, which creates a region of increased evanescent field from the laser source. SERS systems and methods include a device for generating Raman scattered radiation with a detector configured to receive the Raman scattered radiation.

42 Claims, 2 Drawing Sheets

OTHER PUBLICATIONS

Williams, Q.L., et al., "Fast intracavity polarization dynamics of an erbium-doped fiber ring laser: Inclusion of stochastic effects," Physical Review A, vol. 55, No. 3, Mar. 1997, pp. 2376-2386.

Hashiume, Jiro et al.—"Plasmon-enhancement of Optical Near-field of Metal Nanoaperture Surface-emitting Laser"—Applied Physics Letters vol. 84 No. 7 Apr. 26, 2004 pp. 3226-3228.

Viets C et al.—"Single-fibre Surface-enhanced Raman Sensors With Angled Tips" -Journal of Raman Spectroscopy vol. 31 No. 17 Jul. 2000 pp. 625-631.

Moskovits M—Surface-enhanced Spectroscopy—reviews of Modern Physics vol. 57 No. 3 part 1 Jul. 1985 pp. 783-826.

\* cited by examiner

IN SITU EXCITATION FOR SURFACE ENHANCED RAMAN SPECTROSCOPY

FIELD OF THE INVENTION

The present invention relates to chemical analysis using Raman spectroscopy. More particularly, the present invention relates to Surface Enhanced Raman Spectroscopy (SERS) for chemical analysis and combining a radiation source with a SERS analysis structure.

BACKGROUND OF THE INVENTION

Raman Spectroscopy is a well-known spectroscopic technique for performing chemical analysis. In conventional Raman Spectroscopy, high intensity monochromatic light from a light source, such as a laser, is directed onto an analyte to be chemically analyzed. The analyte may contain a single species of molecules or mixtures of different molecules. Furthermore, Raman Spectroscopy may be performed on a number of different molecular configurations, such as organic and inorganic molecules in crystalline or amorphous states.

The majority of the incident photons of the light are elastically scattered by the analyte molecule. In other words, the scattered photons have the same frequency, and thus the same energy, as the photons that were incident on the analyte. However, a small fraction of the photons (i.e., 1 in $10^7$ photons) are inelastically scattered by the analyte molecule at a different optical frequency than the incident photons. The inelastically scattered photons are termed the "Raman effect" and may be scattered at frequencies greater than, but most are usually scattered at a frequency lower than, the frequency of the incident photons. When the incident photons collide with the molecules and give up some of their energy, the Raman scattered photons (also referred to as Raman scattered radiation) emerge with a lower energy. The lower energy Raman scattered photons are commonly referred to in Raman spectroscopy as the "Stokes radiation." A small fraction of the molecules are already in an energetically excited state and when the incident photons collide with the molecules, the Raman scattered photons emerge at a higher energy. The higher energy Raman scattered photons are commonly referred to in Raman spectroscopy as the "anti-Stokes radiation." The Stokes and the anti-Stokes Raman scattered photons are detected by a detector, such as a photomultiplier, resulting in a spectral graph of intensity at a corresponding frequency (i.e., proportional to energy) for the Raman scattered photons. By plotting the frequency of the inelastically scattered Raman photons against intensity, a unique Raman spectrum, which corresponds to the particular analyte molecules, is obtained. This Raman spectrum may be used to identify chemical species, as well as other physical properties of the analyte. While conventional Raman Spectroscopy is suitable for bulk chemical analysis, it is not effective for surface studies because the signal from the bulk Raman scattered photons overwhelms any signal from Raman scattered photons near the surface.

Due to the deficiencies with performing surface studies using conventional Raman Spectroscopy, another Raman Spectroscopy technique called Surface Enhanced Raman Spectroscopy (SERS), which is effective for performing surface studies, has been developed. In SERS, a monolayer of the molecules to be analyzed is adsorbed onto a specially roughened metal surface. Typically, the metal surface is made from gold, silver, copper, lithium, sodium, or potassium. SERS has also been used employing metallic nanoparticles or nanowires for the metal surface, as opposed to a roughened metallic surface. The intensity of the Raman scattered photons from a molecule adsorbed on such a metal surface is typically about $10^4$–$10^6$ greater than conventional Raman Spectroscopy and can be as high as $10^8$–$10^{14}$. Although not thoroughly understood, the selectivity of the surface Raman signal results from the presence of surface enhancement mechanisms and is mainly attributed to two primary mechanisms: electromagnetic enhancement and chemical enhancement, with the electromagnetic enhancement being the dominant mechanism. The enhanced electromagnetic field is highly dependent on the surface roughness features of the metal surface. The chemical enhancement is believed to be dependent on the altered electronic structure of the metal surface due to adsorption of the analyte. The enhanced electromagnetic field of the metallic surface, which is adjacent to the analyte, irradiates the analyte producing an enhanced Raman signal because the strength of the Raman signal is, in part, proportional to the square of the enhanced electromagnetic field. Thus, SERS may be used to study monolayers of materials adsorbed on metals.

Conventionally, lasers have been used as light sources for SERS because of the intensity and narrow wavelength of generated light. However, providing the laser light source and a separate SERS analysis platform create a large and bulky SERS analysis environment. Thus, a device incorporating a laser light source and a SERS analysis surface would be much smaller and allow deposition of the analyte directly on or near the light source. Additionally, it may be beneficial to incorporate the SERS analysis surface on a variety of laser light sources.

BRIEF SUMMARY OF THE INVENTION

The present invention, in a number of embodiments, includes structures and devices for generating Raman scattered radiation, Surface Enhanced Raman Spectroscopy (SERS) systems, and methods of performing SERS.

In one aspect of the present invention, a molecular analysis device comprises a laser source and a SERS-active structure. The laser source may be configured for emanating a laser radiation from an emanating surface of the laser source. The SERS-active structure may be disposed on the emanating surface of the laser source.

In another embodiment of the present invention, a molecular analysis device also comprises a laser source and a SERS-active structure. In this embodiment, the laser source includes a depression formed in the laser source to irradiate a SERS-active structure disposed in the depression at a region of increased evanescent field generated by the active laser source.

Other embodiments of the present invention are SERS systems. The SERS system may include the molecular analysis device wherein the SERS-active structure and analyte may be disposed on the emanating surface, or the SERS system may include the molecular analysis device wherein the SERS-active structure and analyte may be disposed in the depression in the laser source. In either embodiment, the SERS system additionally includes a detector configured and positioned to receive the Raman scattered radiation.

Other embodiments of the present invention include methods for performing SERS. In one method, a laser source configured for emanating the laser radiation on the emanating surface of the laser is provided. A SERS-active structure may be disposed on the emanating surface such that the laser radiation will irradiate the SERS-active structure. An analyte for analysis may be disposed on the SERS-active structure. The method further includes irradiating the analyte and SERS-active structure with the laser radiation, thereby generating Raman scattered radiation, and detecting the Raman scattered radiation.

In another embodiment, the method includes providing a laser source having a depression formed in the laser source. A SERS-active structure may be disposed in the depression such that the laser radiation will irradiate the SERS-active structure. An analyte for analysis may be disposed on the SERS-active structure. The method further includes irradiating the analyte and SERS-active structure with the evanescent field, thereby generating Raman scattered radiation, and detecting the Raman scattered radiation.

Other embodiments of the present invention are also methods for performing SERS. These methods include providing a molecular analysis device including a SERS-active structure, as described above. An analyte may be disposed on the SERS-active structure. The method additionally includes disposing an analyte over at least a portion of the SERS-active structure and irradiating the analyte and SERS-active structure, thereby generating Raman scattered radiation, and detecting the Raman scattered radiation.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes structures and devices for use in Surface Enhanced Raman Spectroscopy (SERS) systems, SERS systems, and methods of performing SERS. As shown in the figures and be described in further detail below, the structures and devices of the present invention are designed to incorporate a SERS-active structure as part of a laser source. In some embodiments, the SERS-active structure may be disposed directly on an emanating surface of the laser source. In other embodiments, a depression may be formed in a portion of the laser source. The depression may be formed to improve an evanescent field emanating from the laser source in the depression. The SERS-active structure may then be disposed in the depression where the evanescent field is stronger. The sensitivity of SERS systems of the present invention may also be enhanced to enable more accurate and sensitive detection of chemical species and other physical properties of the sample being analyzed, including single molecule detection. Furthermore, the SERS systems of the present invention may be employed as analytical instruments for detecting specific chemicals.

Figure 1:
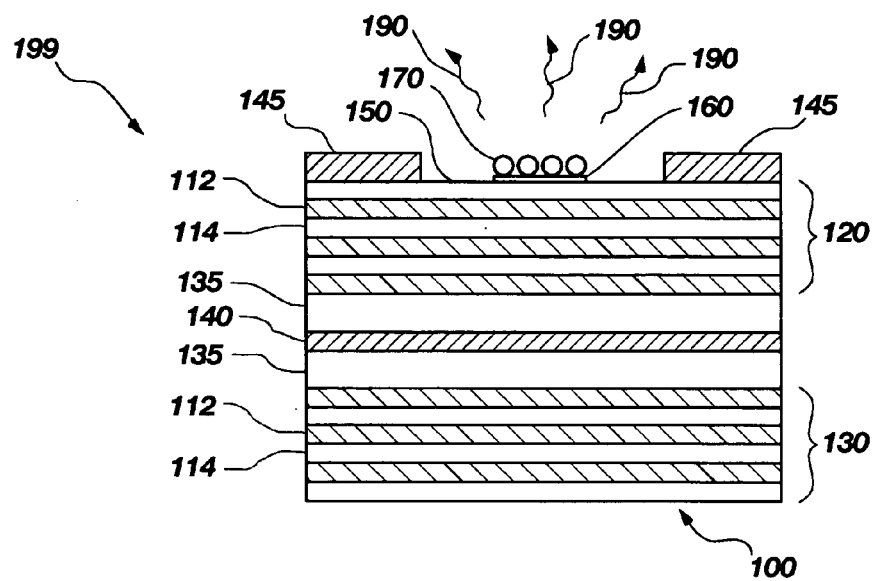
FIG. 1 is a cross section view of an exemplary molecular analysis device using a vertical cavity surface emitting laser.

FIG. 1 depicts a Vertical Cavity Surface Emitting Laser (VCSEL) 100 in a diode configuration and configured as a molecular analysis device 199. VCSELs 100 conventionally include two Bragg reflectors (120 and 130). Bragg reflectors (also referred to as Bragg Mirrors) may be formed in a number of ways using a variety of materials configured as alternating layers having low and high refractive index. Each layer is configured with a thickness of about a quarter wavelength of the light to be generated by the VCSEL 100. The resulting Bragg reflector may also be referred to as a quarter-wave stack. As an example, a Bragg reflector may be formed from alternating layers of GaAs (gallium arsenide) and AlGaAs (aluminum gallium arsenide). Another suitable material combination for forming Bragg reflectors is alternating layers formed respectively from silicon and silicon dioxide. Implementing a larger number of alternating pairs in a Bragg reflector results in a higher refractive index.

In FIG. 1, a bottom Bragg reflector 130 may be formed from alternating first layers 112 and second layers 114. About thirty layers may create a reflectivity as high as 99.99%. A top Bragg reflector 120, through which the laser beam exits, may include about twenty to thirty layers resulting in a reflectivity of about 99.9%. Between the top Bragg reflector 120 and the bottom Bragg reflector 130, a quantum well active region 140 may be formed. The active region 140 may be separated from the top Bragg reflector 120 and the bottom Bragg reflector 130 by spacer layers 135. The spacer layers 135 may be formed with a thickness that creates a very high Q factor optical cavity for amplification of the radiation. An opaque or highly reflective aperture layer 145 may optionally be formed on the top Bragg reflector 120 to create a desired size and shape for the laser radiation 180 leaving the VCSEL 100.

A VCSEL 100 may be electrically pumped or optically pumped (not shown). In an electrically pumped VCSEL 100, the active region 140 may be a material such as InP (Indium Phosphide) and the top Bragg reflector 120 and bottom Bragg reflector 130 may be doped with materials appropriate to create a diode between the top Bragg reflector 120 and the bottom Bragg reflector 130. For example, the bottom Bragg reflector 130 may be doped to create an n-type material and the top Bragg reflector 120 may be doped to create a p-type material. The resulting structure may conventionally be referred to as a P-I-N diode. In this example, the bottom Bragg reflector 130 may be connected to a low voltage potential, while the top Bragg reflector 120 may be connected to a higher voltage potential, thereby biasing the P-I-N diode and causing it to generate laser radiation 180. For clarity, the biasing means have been omitted from FIG. 1.

In an optically pumped VCSEL 100, a portion of an external radiation source (not shown) impinging on the top Bragg reflector 120 or the bottom Bragg reflector 130 may penetrate to the active region 140 where it may be amplified by the high Q optical cavity, thereby generating the laser radiation 180.

A SERS-active structure 160 may be disposed on the emanating surface 150 (and possibly within the aperture if an aperture layer 145 is present) of the VCSEL 100. The SERS-active structure 160 may be used to effect the electromagnetic enhancement of the Raman signal, chemical enhancement of the Raman signal, or both. As used herein, the term "SERS-active structure" means any structure configured and formed of a material that may produce chemical enhancement of the Raman signal, electromagnetic enhancement of the Raman signal, or both. Exemplary materials for the SERS-active structure 160 include gold, silver, copper, aluminum, chromium, lithium, sodium, potassium, or another suitable material that may produce chemical enhancement of the Raman signal, electromagnetic enhancement of the Raman signal, or both. SERS-active structures 160 are more fully described below.

In operation, the SERS-active structure 160 enhances Raman scattered radiation 190, which is generated when the laser radiation 180 irradiates the SERS-active structure 160 and analyte 170 disposed on the SERS-active structure 160.

Figure 2:
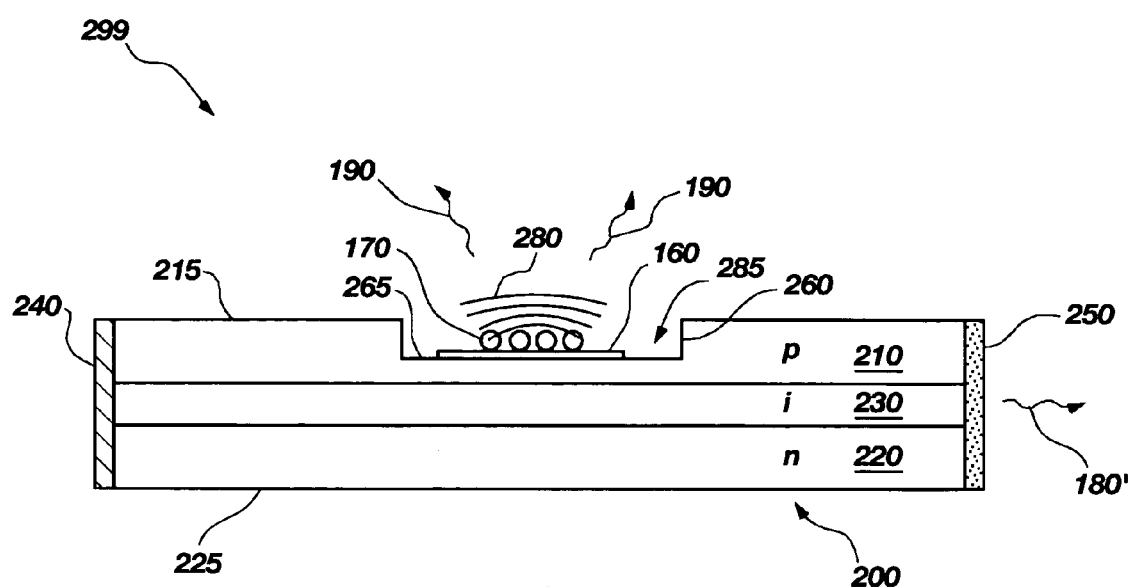
FIG. 2 is a cross section view of an exemplary molecular analysis device using an edge emitting laser.

FIG. 2 depicts an edge-emitting laser 200 in a diode configuration, which acts as a molecular analysis device 299 according to the present invention. In a conventional diode configuration of an edge emitting laser 200, an active layer 230 separates a p-type layer 210 from an n-type layer 220. When the laser diode configuration is biased with a positive voltage between the p-type layer 210 and n-type layer 220 (by means not shown), an electrically pumped light emitting diode action is created in the active layer 230. The edge emitting laser 200 may include reflectors within the p-type layer 210 and the n-type layer 220 to contain the generated laser radiation 180' and enhance the optical waveguide characteristics of the active layer 230 separated by the p-type layer 210 and the n-type layer 220. These reflectors may be structures such as distributed Bragg reflectors (described above) and distributed Bragg gratings. The active layer 230 may also contain one or more quantum wells for enhancing generation of the laser radiation 180'. Conventionally, the ends of the edge emitting laser 200 may be cleaved to form smooth parallel edges. These cleaved edges are somewhat transmissive and somewhat reflective. Due to the reflective property, the cleaved edges form a Fabry-Perot cavity to contain and assist in amplification of the laser radiation 180'. In many embodiments, one of the cleaved edges may be coated with a more reflective material creating a relatively reflective cleaved edge 240, thereby preventing a substantial amount of the laser radiation 180' from emanating from the reflective cleaved edge 240. As a result, most of the laser radiation 180' emanates from the uncoated relatively transmissive cleaved edge 250 (also referred to as an emanating surface) having a more transmissive property.

The edge emitting laser 200 shown in FIG. 2 is a basic configuration for discussion purposes; other more complex forms of diode edge emitting lasers 200, such as ridge laser structures and buried heterostructures, are possible. Additionally, as with the VCSEL 100, edge emitting lasers 200 may be constructed containing the Fabry-Perot cavity using Bragg reflectors on the top and bottom, but without the diode structure. An edge emitting laser 200 formed in this fashion may use a light pump beam (not shown) incident on one of the lateral surfaces (215 and 225), which penetrates through the Bragg reflectors to generate the laser radiation 180' in the active layer 230. These more complex forms of edge emitting lasers 200 are also contemplated as being within the scope of the present invention In one embodiment using the edge emitting laser 200, similar to the VCSEL 100, a SERS-active structure 160 may be disposed on the emanating surface 150 (shown in FIG. 1) (i.e., the transmissive cleaved edge 250) of the edge emitting laser 200 (not shown).

In another embodiment, as shown in FIG. 2, the edge emitting laser 200 may include a depression 260 formed in either a lateral surface 215 of the p-type layer 210 or a lateral surface 225 of the n-type layer 220. FIG. 2 depicts the depression 260 in the lateral surface 215 of the p-type layer 210. However, the depression 260 may also be formed in the lateral surface 225 of the n-type layer 220. Additionally, for simplicity, the depression 260 is shown with a flat analysis surface 265 and with perpendicular walls forming the sides of the depression 260. However, it may be advantageous to form the depression 260 with curved walls and a flat analysis surface 265 or as a curved analysis surface 265 formed in the lateral surface 215, using any suitable shape, such as a portion of an ellipsoid or paraboloid.

Radiation sources, such as edge emitting lasers 200, have an evanescent field 280 emanating from the radiation source. The evanescent field 280 generally decays exponentially as it emanates and propagates away from the radiation source. Forming the depression 260 may create an analysis surface 265 in a region of increased evanescent field 285 emanating from the radiation source. Accordingly, the depression 260 can bring the analysis surface 265 closer to the laser source where the evanescent field 280 may be stronger. Formation and size of the depression 260 can be used to influence the electrical and reflective properties of the edge emitting laser 200 and to provide an increased evanescent field 280 for the analysis surface 265.

With the depression 260 created, a SERS-active structure 160 may be disposed in the depression 260. The SERS-active structure 160 may be used to effect the electromagnetic enhancement of the Raman signal, chemical enhancement of the Raman signal, or both. The SERS-active structure 160 enhances Raman scattered radiation 190 generated when the evanescent field 280 irradiates the SERS-active structure 160 and the analyte 170 disposed on the SERS-active structure 160. The SERS-active structure 160 is explained more fully below.

Figure 3:
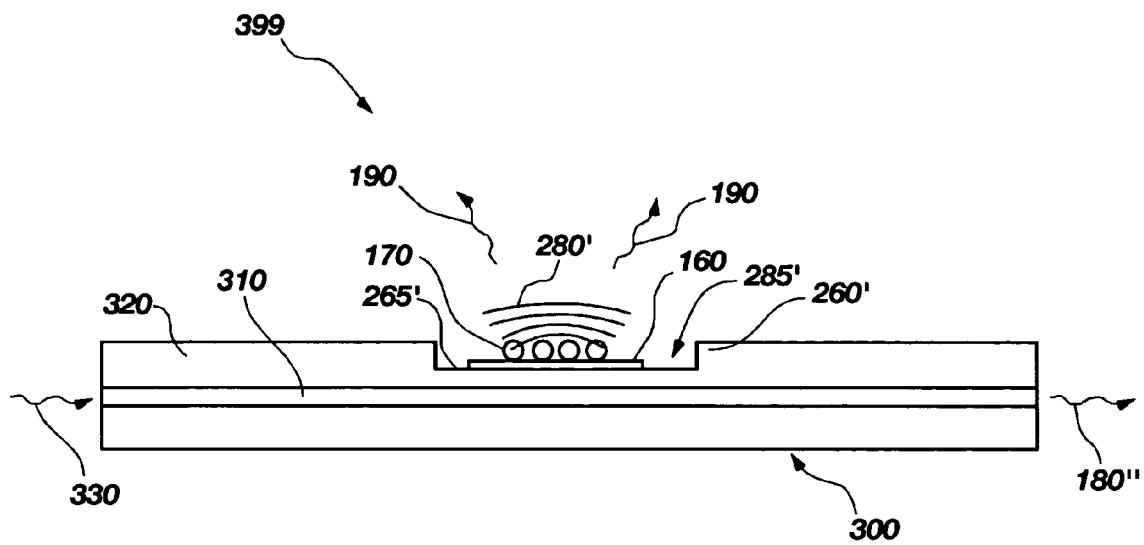
FIG. 3 is a cross section view of an exemplary molecular analysis device using a fiber laser.

FIG. 3 shows a fiber laser 300 configured as a molecular analysis device 399, according to an embodiment of the invention. Fiber lasers 300 comprise a fiber optic element with a doped core 310, which may be doped with a rare earth element, such as, for example, erbium, neodymium or any other elements that cause an optical gain. The doped core 310 is encased in a reflective cladding 320 to direct and confine optical radiation within the doped core 310. The optical cavity created in the doped core 310 of a fiber laser 300 may create a long resonator cavity enhancing the optical gain such that an optical doped fiber may generate laser radiation 180" when optically pumped with a pump radiation source 330 directed at the doped core 310. As with the edge emitting laser 200, a fiber laser 300 may include an evanescent field 280' that decays as it emanates and propagates away from the radiation source. A depression 260' may be formed in the fiber laser 300 by removing a portion of the cladding 320 in a selected area. The depression 260' creates an analysis surface 265' in a region of increased evanescent field 285' emanating from the radiation source. Size and depth of the depression 260' can provide an increased evanescent field 280' for the analysis surface 265' and influence the reflective properties of the cladding 320, and thereby the optical gain of the fiber laser 300.

For simplicity, the depression 260' is shown with a flat analysis surface 265' and with perpendicular walls forming the sides of the depression 260'. However, it may be advantageous to form the depression 260' with curved walls and a flat analysis surface 265' or as a curved analysis surface 265' formed in the cladding 320, using any suitable shape, such as a portion of an ellipsoid or paraboloid.

With the depression 260' created, a SERS-active structure 160 may be disposed in the depression 260'. The SERS-active structure 160 may be used to effect the electromagnetic enhancement of the Raman signal, chemical enhancement of the Raman signal, or both. The SERS-active structure 160 enhances Raman scattered radiation 190 generated when the evanescent field 280' irradiates the SERS-active structure 160 and analyte 170 disposed on the SERS-active structure 160.

The SERS-active structure 160 may be used in any of the laser embodiments described above. It has been shown that a relatively rough surface enhances the amount of Raman scattered radiation 190 that may emanate from the SERS-active structure 160 when an analyte 170 disposed on the SERS-active structure 160 is irradiated. As a result, the SERS-active structure 160 may be formed as a single monolithic layer, possibly with a roughened surface, or the SERS-active structure 160 may comprise one or more discrete particles.

As a layer, the SERS-active structure 160 may be disposed on an analysis surface 265. The analysis surface 265 may be in the depression 260', for embodiments including a depression 260, or on the emanating surface 150, for embodiments without the depression 260. The SERS-active structure 160 may be disposed by chemically bonding or merely disposing on the analysis surface 265 and weakly bonding thereto, if bonded at all.

As one or more discrete particles, the SERS-active structure 160 may have a variety of exemplary configurations, such as, nanowires (i.e., a rod shaped configuration), nanodots, nanoparticles (including employing a single nanoparticle), or metallic particles in a colloidal suspension. Representative nanostructures may range in size from less than about 10 nm to more than about 1000 nm. It is currently preferred to employ at least two silver nanoparticles spaced apart such that an analyte 170 molecule may be draped therebetween. The spacing of the nanoparticles may depend on the shape of the nanostructure and can be from about 1 nanometer to greater than about 100 nanometers and also depends on the molecule. The aforementioned nanostructures for the SERS-active structure 160 may be formed by chemical vapor deposition (CVD), molecular beam epitaxy (MBE), atomic layer deposition (ALD), or any other suitable technique to deposit the SERS-active structure 160 on the analysis surface 265.

In a particular embodiment of the invention, receptors may be used with the analyte. The receptors can be used to selectively bind a specific analyte to the SERS active structure to selectively detect certain species.

Figure 4:
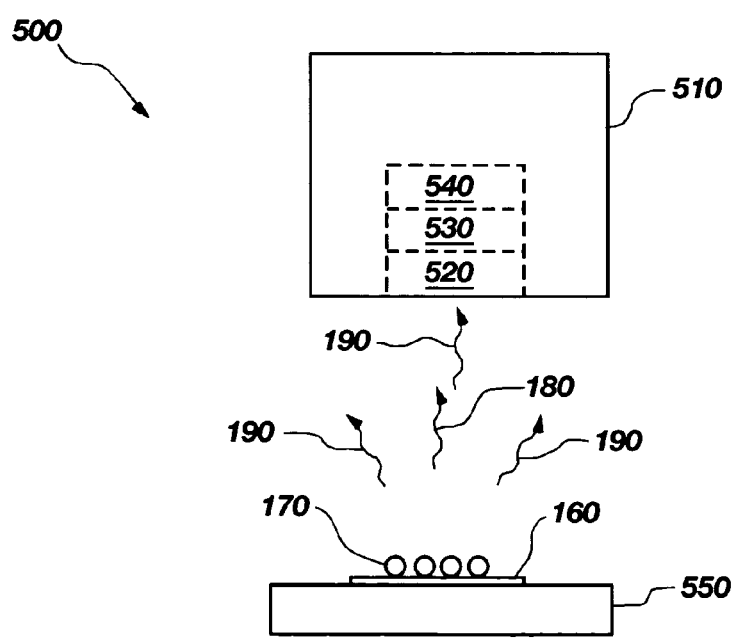
FIG. 4 shows a SERS system including the molecular analysis device according to one embodiment of the present invention.

In FIG. 4, an exemplary SERS system 500 includes a molecular analysis device (199, 299, and 399) and a detector 510. The molecular analysis device (199, 299, 399) may be any of the embodiments discussed above. The Raman scattered radiation 190 (i.e., photons) may be collected by a lens 520 or lens assembly. The wavelengths that are emitted by the light source employed in the SERS system 500 of the present invention may be any suitable wavelength for properly analyzing the analyte 170. For example, a representative range for the wavelengths that may be emitted by the light source are about 350 nm to about 1000 nm.

In operation of the SERS system 500, the radiation source 550 (e.g., a VCSEL 100, an edge emitting laser 200, or a fiber laser 300) irradiates the SERS-active structure 160 and analyte 170 producing a surface enhancement effect therein (i.e., chemical, electromagnetic, or both). In other words, irradiation of the SERS-active structure 160 and analyte 170 by radiation impinging on the SERS-active structure 160 and analyte 170, in part, produces a strong electromagnetic field in the SERS-active structure 160. Because the electromagnetic field is adjacent to the analyte 170, the analyte 170 is, in turn, irradiated by a very strong electromagnetic field. The irradiation of the analyte 170 by the enhanced field from the SERS-active structure 160 produces the aforementioned Stokes, anti-Stokes, or combined (Stokes/anti-Stokes), Raman scattered photons 190 (also referred to as Raman scattered radiation) that are characteristic of the particular analyte 170 being analyzed. Because the intensity of the Raman scattered photons 190 is, in part, proportional to the square of the electromagnetic field that irradiates the analyte 170, the enhancement effect from the SERS-active structure 160 may increase the intensity of the Raman signal by as much as $10^{14}$.

Ideally, the Raman scattered photons 190 are isotropic, being scattered in all directions. If the scattering is isotropic, the position of the detector 510 is not particularly important. However, if the wavelength of the radiation emanating from the radiation source 550 is close to the wavelength of the Raman scattered photons 190, a more optimal positioning of the detector 510 may be used, as shown in FIG. 4, with the detector 510 positioned in substantially the same axis as the direction of the laser radiation 180. It should be understood that the detector 510 may include a monochromator 530 or another suitable device for determining the wavelength of the Raman scattered photons 190 and a device, such as, for example, a photomultiplier for determining the intensity of the emitted Raman scattered photons 190. A filter 540 or a plurality of filters 540 may be employed, either included with the structure of the detector 510 or as a separate unit, that is configured to filter 540 the wavelength of the light from the light source, thus, allowing only the Raman scattered photons 190 to be received by the detector 510.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A molecular analysis device, comprising:
    a laser source configured for emanating a laser radiation from an emanating surface of the laser source; and
    a SERS-active structure disposed on the emanating surface and configured to produce a Raman scattered radiation when the laser radiation irradiates
    an analyte disposed on the SERS-active structure.

2. The device of claim 1, wherein the laser source is a vertical cavity surface emitting laser.

3. The device of claim 1, wherein the laser source is an edge emitting laser.

4. The device of claim 1, wherein the laser source is electrically pumped or optically pumped.

5. The device of claim 1, wherein the SERS-active structure comprises a metallic material selected from the group consisting of gold, silver, copper, aluminum, chromium, lithium, sodium, and potassium.

6. The device of claim 5, wherein the SERS-active structure is substantially roughened to increase a surface enhancement effect of the Raman scattered radiation.

7. The device of claim 1, wherein the SERS-active structure comprises a colloid containing metallic particles, wherein the metallic particles are selected from the group consisting of gold, silver, copper, aluminum, chromium, lithium, sodium, and potassium.

8. The device of claim 1, wherein the SERS-active structure comprises a plurality of nanostructures including a metallic material, wherein the plurality of nanostructures are selected from the group consisting of, nanodots or nanowires.

9. The device of claim 8, wherein the metallic material is selected from the group consisting of gold, silver, copper, aluminum, chromium, lithium, sodium, and potassium.

10. A molecular analysis device, comprising:
a laser source having a depression formed in the laser source exposing a region of increased evanescent field generated when the laser source is active; and
a SERS-active structure disposed in the depression and configured to produce a Raman scattered radiation when the evanescent field irradiates an analyte disposed on the SERS-active structure.

11. The device of claim 10, wherein the laser source is an edge emitting laser.

12. The device of claim 11, wherein the depression is formed by removing at least a portion of a lateral surface of the edge emitting laser.

13. The device of claim 11, wherein the laser source is electrically pumped or optically pumped.

14. The device of claim 10, wherein the laser source is a fiber laser.

15. The device of claim 14, wherein the depression is formed by removing at least a portion of a cladding from the fiber laser.

16. The device of claim 10, wherein the SERS-active structure comprises a metallic material selected from the group consisting of gold, silver, copper, aluminum, chromium, lithium, sodium, and potassium.

17. The device of claim 16, wherein the SERS-active structure is substantially roughened to increase a surface enhancement effect of the Raman scattered radiation.

18. The device of claim 10, wherein the SERS-active structure comprises a colloid including metallic particles, wherein the metallic particles are selected from the group consisting of gold, silver, copper, aluminum, chromium, lithium, sodium, and potassium.

19. The device of claim 10, wherein the SERS-active structure comprises a plurality of nanostructures including a metallic material, wherein the plurality of nanostructures are selected from the group consisting of nanodots or nanowires.

20. The device of claim 19, wherein the metallic material is selected from the group consisting of gold, silver, copper, aluminum, chromium, lithium, sodium, and potassium.

21. A surface enhanced Raman spectroscopy (SERS) system, comprising:
a molecular analysis device, comprising:
a laser source configured for emanating a laser radiation from an emanating surface of the laser source; and
a SERS-active structure disposed on the emanating surface and configured to produce a Raman scattered radiation when the laser radiation irradiates an analyte disposed on the SERS-active structure; and
a detector configured and positioned to receive the Raman scattered radiation.

22. The system of claim 21, wherein the detector further comprises a filter configured to substantially block a frequency of the laser radiation.

23. A surface enhanced Raman spectroscopy (SERS) system, comprising:
a molecular analysis device, comprising:
a laser source having a depression formed in the laser source exposing a region of increased evanescent field generated when the laser source is active; and
a SERS-active structure disposed in the depression and configured to produce a Raman scattered radiation when the evanescent field irradiates an analyte disposed on the SERS-active structure; and
a detector configured and positioned to receive the Raman scattered radiation.

24. The system of claim 23, wherein the detector further comprises a filter configured to substantially block a frequency of the evanescent field.

25. A method of performing surface enhanced Raman spectroscopy (SERS), comprising:
providing a laser source configured for emanating a laser radiation from an emanating surface on the laser source;
providing a SERS-active structure disposed on the emanating surface and configured such that the laser radiation irradiates the SERS-active structure;
disposing an analyte over at least a portion of the SERS-active structure;
irradiating the analyte and the SERS-active structure with the laser radiation to generate a Raman scattered radiation; and
detecting the Raman scattered radiation.

26. The method of claim 25, wherein disposing the analyte comprises disposing at least one molecule of the analyte.

27. The method of claim 25, wherein detecting the Raman scattered radiation comprises:
providing a detector positioned with respect to the SERS-active structure to receive the Raman scattered radiation; and
substantially filtering a frequency of the laser radiation from being received by the detector.

28. The method of claim 25, further comprising, selecting the SERS-active structure to comprise a metallic material selected from the group consisting of gold, silver, copper, aluminum, chromium, lithium, sodium, and potassium.

29. The method of claim 25, further comprising, selecting the SERS-active structure to comprise a colloid including metallic particles selected from the group consisting of gold, silver, copper, aluminum, chromium, lithium, sodium, and potassium.

30. The method of claim 25, further comprising, selecting the SERS-active structure to comprise at least one particle in the form of a nanodot or a nanorod.

31. A method of performing surface enhanced Raman spectroscopy (SERS), comprising:
providing a laser source configured with a depression formed in the laser source at a region of increased evanescent field generated by the laser source;
providing a SERS-active structure disposed in the depression and configured such that the evanescent field irradiates the SERS-active structure;
disposing an analyte over at least a portion of the SERS-active structure;
irradiating the analyte and the SERS-active structure with the evanescent field to generate a Raman scattered radiation; and
detecting the Raman scattered radiation.

32. The method of claim 31, wherein disposing the analyte comprises disposing at least one molecule of the analyte.

33. The method of claim 31, wherein detecting the Raman scattered radiation comprises:
   providing a detector positioned with respect to the SERS-active structure to receive the Raman scattered radiation; and
   substantially filtering a frequency of the evanescent field from being received by the detector.

34. The method of claim 31, further comprising, selecting the SERS-active structure to comprise a metallic material selected from the group consisting of gold, silver, copper, aluminum, chromium, lithium, sodium, and potassium.

35. The method of claim 31, further comprising, selecting the SERS-active structure to comprise a colloid including metallic particles selected from the group consisting of gold, silver, copper, aluminum, chromium, lithium, sodium, and potassium.

36. The method of claim 31, further comprising, selecting the SERS-active structure to comprise at least one particle in the form of a nanodot or a nanorod.

37. A method of performing surface enhanced Raman spectroscopy (SERS), comprising:
   providing a molecular analysis device comprising:
      a laser source configured for emanating a laser radiation from an emanating surface of the laser source; and
      a SERS-active structure disposed on the emanating surface;
   disposing an analyte over at least a portion of the SERS-active structure;
   irradiating the analyte and the SERS-active structure with the laser radiation to generate a Raman scattered radiation; and
   detecting the Raman scattered radiation.

38. The method of claim 37, wherein disposing the analyte comprises disposing at least one molecule of the analyte.

39. The method of claim 37, wherein detecting the Raman scattered radiation comprises:
   providing a detector positioned with respect to the SERS-active structure to receive the Raman scattered radiation; and
   substantially filtering a frequency of the laser radiation from being received by the detector.

40. A method of performing surface enhanced Raman spectroscopy (SERS), comprising:
   providing a molecular analysis device, comprising:
      a laser source having a depression formed in the laser source exposing a region of increased evanescent field generated when the laser source is active; and
      a SERS-active structure disposed in the depression;
   disposing an analyte over at least a portion of the SERS-active structure; and
   irradiating the analyte and the SERS-active structure with the evanescent field to generate a Raman scattered radiation; and
   detecting the Raman scattered radiation.

41. The method of claim 40, wherein disposing the analyte comprises disposing at least one molecule of the analyte.

42. The method of claim 40, wherein detecting the Raman scattered radiation comprises:
   providing a detector positioned with respect to the SERS-active structure to receive the Raman scattered radiation; and
   substantially filtering a frequency of the evanescent field from being received by the detector.

* * * * *